United States Patent [19]

Gough

[11] 4,335,105
[45] Jun. 15, 1982

[54] SPECIFIC ANTIGEN VACCINE FOR TGE IN SWINE

[75] Inventor: Patricia M. Gough, Ames, Iowa

[73] Assignee: Iowa State University Research Foundation, Inc., Ames, Iowa

[21] Appl. No.: 262,768

[22] Filed: May 11, 1981

Related U.S. Application Data

[63] Continuation-in-part of Ser. No. 253,070, Apr. 10, 1981, abandoned, which is a continuation of Ser. No. 93,070, Nov. 13, 1979, abandoned.

[51] Int. Cl.$^3$ .................... A61K 39/12; A61K 39/215
[52] U.S. Cl. ................................ 424/89; 260/112 R; 435/239
[58] Field of Search ......................... 424/89; 435/239; 260/112

[56] References Cited

U.S. PATENT DOCUMENTS

| | | |
|---|---|---|
| 3,479,430 | 11/1969 | Welter . |
| 3,585,108 | 6/1971 | Welter . |
| 3,823,228 | 7/1974 | Ferris et al. . |
| 4,158,054 | 6/1979 | Furminger et al. .................. 424/89 |
| 4,190,645 | 2/1980 | Almeida .............................. 424/89 |

OTHER PUBLICATIONS

Garwes, D. J. et al., The Polypeptide Structure of Transmissible Gastro-enteruis Virus, J. Gen. Virol., (A75) 29(1):25–34 as abstracted in Vet. Bull. 46(3), 1326 (1976), ca, 84# 27843y, (1976).

Stone, S. S. et al., Partial Characterization of the Principal Soluble Antigens Associated with The Coronavirus of Transmissible Gastroenteritis by Complement Fixation and Immunodiffusion Infection and Immunity (1976), 13(2):521–526, as abstracted Vet. Bull., 46# 4383, (1976).

Garwes, D. J. et al., Antigenicity of Structural Components from Porcine Transmissible Gastroenteritis Virus Veterinary Microbiology, 1979 (3) (3) 179–190 as abstracted in Vet. Bull. 49(9) 5247, Sep. 1979.

Wege, H. et al., J. Gen. Virol, 1979, 42(1):37–47 as abstracted C.A. 90:99776A, (1979).

MacNaughton, Mr. Arch, Virol., 1980, 63(1):75–80 as abstracted C.A. 92: 107007J, (1980).

Bohl et al., Infection and Immunity, 6, 289–301, (Sep. 1972).

Bohl et al., Infection and Immunity, 11, 23–32, (Jan. 1975).

Garwes et al., Journal General Virology, 32, 283–294, (1976).

Tamoglia, J. A. V. M. A., 160, 554–558, (1972).

Gough et al., Abstracts of Papers Presented at Conference of Research Workers in Animal Diseases, 57th Ann. Meeting, Abstract 62, p. 11, (Nov. 29–30, 1976).

*Primary Examiner*—Shep K. Rose

[57] ABSTRACT

A vaccine for protecting swine against transmissible gastroenteritis (TGE) is prepared from a specific antigenic protein (SPA) obtained by separation from TGE virus. The SPA is characterized by a buoyant density of 1.02 to 1.03 gms/ml in a solution of sucrose. The vaccine may be prepared in parenteral dose form for administration to pregnant sows, thereby effectively protecting the baby pigs against fatal TGE infection.

10 Claims, No Drawings

SPECIFIC ANTIGEN VACCINE FOR TGE IN SWINE

RELATED APPLICATIONS

This application is a continuation-in-part of copending application Ser. No. 253,070, filed Apr. 10, 1981, entitled "Specific Antigen Vaccine for TGE in Swine," which was a continuation of application Ser. No. 93,070, filed Nov. 13, 1979, and both now abandoned.

BACKGROUND AND PRIOR ART

Transmissible gastroenteritis (TGE) of swine is caused by a coronavirus (TGEV). The disease occures wherever swine are raised, and it is highly fatal for baby pigs during the first few weeks after farrowing. However, if the sow has had a recent TGE infection, protective antibodies are transferred to the offspring in the colostrum and milk which protect the baby pigs against TGE. Bohl et al, *Infect. & Immun.*, 6, 289–230 (1972). TGE vaccines have been developed which are capable of producing high serum virus neutralizing titers to TGEV. Such vaccines are prepared from attenuated, non-virulent TGEV, strains of which may be prepared by continuous cell culture of virulent TGEV. See, for example, U.S. Pat. Nos. 3,479,430 and 3,585,108. However, such vaccines are not very effective in producing lactogenic immunity in the sow, whether the attenuated TGEV is given live or inactivated. Tamoglia, J.A.V.-M.A., 160, 554–558 (1972).

Studies have shown that IgA antibodies are produced in milk by TGE infection or by administration of live virulent TGEV, while the administration of attenuated vaccines produces mainly IgG antibodies. Bohl et al, *Infect. & Immun.*, 11, 23–32 (1975). Bohl et al suggest that effective passive immunization of baby pigs may depend on continual neutralization of virus within their intestinal tracts by the IgA antibodies produced in milk after exposure of the sow to virulent TGE. However, vaccines containing virulent TGEV would be hazardous to use, since the virus is readily transferred among swine in a herd.

SUMMARY OF INVENTION

Coronaviruses have been reported as containing from four to sixteen different proteins, which are in the form of polypeptides, some of which are glycosylated. Wege et al, *J. Gen. Virol.*, 42, 37–47 (1979). For example, Wege et al analyzed the proteins of the murine coronavirus and found that it contained six proteins, two of which were glycoproteins, and that the protein components ranged in molecular weight from about 170,000 to 22,700. A preliminary report on the purification and fractionation of the proteins of TGE virus was presented by Gough and Ellis to the 1976 Conference of Research Workers in Animal Disease at Chicago, Ill. An Abstract of the Gough and Ellis paper was published: Abstracts of Papers Presented at Conference of Research Workers in Animal Disease, 57th Annual Meeting Nov. 29–30, 1976, p. 11. The discoveries on which the present invention are based occurred subsequent to 1976, which were not made public prior to the filing of this application.

This invention is based in part on the discovery that an important antigenic factor is at least partially lost in the recovery of TGE virus for use in vaccines. This antigenic factor appears to be a protein associated with the surface of the virus from which it is easily separated by mechanical attrition, such as would occur when the TGE virus is subjected to sonication during a recovery procedure. For the purpose of the present invention, this antigenic factor is designated as "TGE-SPA" or as "SPA", since it is believed to be a specific protein antigen for protection of swine against TGE. The quantity of the SPA factor associated with TGEV appears to be reduced by attenuation, that is, virulent strains of TGE are believed to contain relatively more of the SPA than do attenuated strains. Possibly, the failure of attenuated strain vaccines to produce the same level of lactogenic immunity as obtained by natural TGE infection or by experimental injection of virulent TGEV in breeding sows is related to this difference.

The present invention is further based on the findings that the TGE-SPA for use in preparing vaccines in accordance with the present invention may be readily separated from TGEV or other sub-viral protein components of TGE, and that the SPA may be identified by physical criteria which characterize specific protein molecules, such as buoyant density and electrophoretic mobility. This SPA factor and the vaccines which can be prepared therefrom will now be described in detail.

DETAILED DESCRIPTION

The TGE-SPA immunogen for use in practicing the present invention is prepared from TGEV, which has been replicated in the small intestines of baby pigs or in pig cell culture. Since virulent strains of TGEV appear to contain more of the desired specific antigen, it is preferred to use virulent TGEV. However, the SPA can also be obtained from TGEV which has been adapted to cell culture. If the virus is to be propagated in cell culture it may be advantageous to use the adapted, less virulent virus. In general, however, it is preferred to infect the cells with TGEV which is capable of causing TGE in swine. For example, the Illinois isolant of TGEV may be used as the virus for replication either in vivo in the pig intestine, or in vitro in a culture of swine cells such as testes cells. The Illinois isolant is a standard laboratory virus, and can be obtained from the Veterinary Services Laboratory, U.S.-D.A., Ames, Iowa, and other sources. Other suitable virulent isolants can readily be obtained from the intestines of pigs naturally infected with TGE.

The TGEV is isolated from the culture medium. For example, the jejunum of the samll intestines of the pig may be subdivided, such as by grinding, and a suspension formed therefrom in a suitable aqueous medium. Similarly, the cultured cells may be suspended in a suitable medium for further processing. The suspension is subjected to centrifugation to remove the intestinal or cellular debris. The supernatant contains the TGEV. The virus is precipitated from the supernatant by a suitable precipitating agent such as polyethylene glycol or ammonium sulfate. On completion of the precipitation, the precipitate is collected by centrifugation, for example, at 9500 g for 30 minutes. The separated precipitate is then redispersed in a suitable aqueous medium for further purification. For example, this can be accomplished by rate-zonal centrifugation through a discontinuous sucrose density gradient. The buoyant density of the TGEV precipitated with polyethylene glycol 6000 is 1.122 gms/ml. The virus will therefore sediment through 10, 25, and 40% discontinuous sucrose gradients to the 25–40% sucrose interface.

The virus-containing band is separated. At this point, the desired SPA is still associated with the TGEV, apparently being a constituent of the surface of the TGE virion. To liberate the SPA, mechanical energy may be applied to the virus. One preferred procedure is to subject the TGEV suspension to sonication. As the SPA is broken off it goes into solution. The desired viral protein is therefore characterized in one respect by its watersolubility.

The sonicated suspension of the TGEV may contain two viral proteins in solution both of which have buoyant densities of 1.02 to 1.03 grams per milliliter (gms/ml). These proteins can therefore be separated and recovered from the residual TGEV by isopycnic centrifugation using a continuous sucrose density gradient. For example, the isopycnic centrifugation may be carried out using a gradient of 10 to 60% sucrose for 18-20 hours at 260,000 g. The second band of material, which may be referred to as "Band B", corresponding to about 6 to 8% sucrose, will contain the SPA together with the other protein component. The separated Band B may be used directly to form a vaccine in accordance with the present invention, or it may be further purified to increase the concentration of the SPA relative to the other protein.

For example, on a laboratory basis, the Band B protein solution may be further purified by gel filtration using a column of Sepharose 4B or Sephadex G200. Applying a tris-saline buffer as the eluant, the desired immunogen (TGE-SPA) will be the second fraction to be eluted, the first fraction containing the other protein of similar buoyant density. Where this concentration is above that desired for the vaccine, the eluate may be diluted to the concentration for preparing the vaccine. Alternatively, where the concentration of the eluate is below that desired for the vaccine, the SPA may be concentrated by procedures such as electrophoresis, ultrafiltration, endosmosis or precipitation and resuspension such as with polyethylene glycol or other precipitating agents. For commercial production, techniques other than isopycnic centrifugation and gel filtration may be employed for isolating the SPA.

The SPA protein which is used as the immunogen in vaccines of the present invention has been further characterized by its electrophoretic mobility, which is referred to as the Rf value. The Rf value is determined under charge-neutralized conditions, such as in the presence of sodium dodecyl sulfate, and is relative to human serum albumin by polyacrylamide gel electrophoresis. Under these conditions in the presence of urea, the Rf value of the SPA protein component is 1.84±0.01. The similarly determined Rf value in the absence of urea is 0.99±0.01. Molecular weights calculated from these Rf values give approximate molecular weights of 25,000 corresponding to Rf. 1.84 and 67,000 corresponding to Rf. 0.99. The probable explanation for these different values is explained below in Example IV.

The SPA immunogen prepared in accordance with the present invention is preferably free of TGE virus. It may be in admixture with the other viral protein such as protein of the same buoyant density, as obtained in the form of Band B. However, further purification may be desirable so that the final vaccine immunogen is composed substantially entirely of the SPA protein. For example, 90% or more of the protein of the immunogen may be the SPA protein which is water-soluble, has a buoyant density of 1.02 to 1.03 gms/ml, a charge-neutralized electrophoretic mobility (Rf value) of 1.84±0.01 relative to human serum albumin in the presence of urea, and 0.99±0.01 in the absence of urea, and an isolectric point of pH 3.8 corresponding to the Rf. 0.99 form of the SPA.

The SPA immunogen can be prepared in vaccine dose form by well known procedures. For parenteral administration, such as intramuscular injection, the SPA is combined with a suitable adjuvant. Aluminum hydroxide has been found to be a desirable adjuvant. Aluminum hydroxide adjuvants can be prepared as described in U.S. Pat. No. 3,149,036, or obtained from a commercial source, such as Merck Adjuvant 65, of Merck & Co., Inc., Rahway, N.J. Other standard adjuvants can also be used such as Freund's Incomplete Adjuvant, which can be obtained from Difco Laboratories, Detroit, Mich. The relative proportions of SPA immunogen and adjuvant can be varied, providing both are present in effective amounts. For example, the aluminum hydroxide adjuvant may be present in an amount of 0.5% of the vaccine mixture ($Al_2O_3$ basis). On a per dose basis, the concentration of the SPA immunogen may range from 0.25 to 4.0 milligrams (mg), but is preferably within the range from about 0.5 to 3.0 mg per dose. For example, good results are obtained with intramuscular administration of 1.0 to 2.0 mg of SPA per dose to pregnant sows for protection of the baby pig offspring. A convenient dose size is about one milliliter. Therefore, a representative dose for intramuscular injection would comprise 1 ml containing 1.0 mg of SPA in admixture with 0.5% aluminum hydroxide adjuvant. Similar dose forms may also be prepared for parenteral administration to baby pigs, but the amount of SPA given per dose may be smaller such as 0.25 to 1.0 mg per dose. The SPA immunogen may also be prepared in the form of an enteric-coated oral vaccine, for example, as described in U.S. Pat. No. 3,823,228.

The mechanism of action of the SPA vaccines is not fully understood. For passive immunization of baby pigs, it appears that the pregnant sow is stimulated to produce the required immunizing antibodies in the colostrum and milk. However, because of the small size of the SPA molecule, it is possible that some of the antigen is transferred through the placenta to the baby pigs, thereby stimulating direct production of immunity in the baby pigs prior to or immediately following birth. Not only is the vaccine highly effective for such passive immunization but it has the advantage of being entirely safe to use. There is no possibility of TGE infection being caused by the vaccine, as where live virulent TGE virus are used. Further, as compared with TGE vaccines prepared from attenuated non-virulent strains of TGEV, the SPA vaccines are much more effective for passive immunization of baby pigs. Another important advantage of the SPA vaccines is that they can be used as part of a program for TGE eradication. The antibodies produced by SPA vaccination can be distinguished from the antibodies produced by natural TGE infection, and therefore infected swine can be distinguished from immunized vaccinated swine.

The practice of this invention and the results which can be obtained thereby are further illustrated by the following examples.

EXAMPLE I

The TGE-SPA immunogen for use in preparing vaccines in accordance with the present invention may be prepared as follows:

1. The TGEV is produced from the virulent Illinois isolant of TGEV, which is replicated in small intestines of baby SPF pigs (infected at 48 hrs of age, virus generally harvested 48 hrs post-infection). A 20% suspension of the ground jejunum of the infected pigs is made in minimum essential medium (Eagle's) to which 5% lactalbumin hydrolysate, 2% fetal porcine serum and antibiotics have been added. Alternatively, the Illinois isolant is replicated in roller cultures of swine testes cells. The cells are 6-day-old (post-passage) monolayers when infected and harvest of virus is done at 3 days post-inoculation. Higher titers of virus are obtained with older cells (6 to 8 days) than with younger (3 to 5 days) cells. This is especially important with strains of TGE virus (such as Illinois) which are not well-adapted to in vitro conditions. Virus is collected after two freeze-thaw cycles of cells-medium.

2. The crude virus is centrifuged at approximately 5000 g for 20 to 30 minutes to remove cellular or intestinal debris.

3. The virus is precipitated from the supernatant by adding 7% polyethylene glycol 6000 and 2.3% sodium chloride. The mixture is held at 40° C. for 1.5 to 2.5 hours for precipitation to be completed.

4. The precipitate is collected by centrifugation at 9500 g for 30 min. The precipitate is dispersed in Eagle's minimum essential medium, pH 7.0, to a volume 1/20th of the original.

5. The dispersion is subjected to rate-zonal centrifugation through a discontinuous (10, 25, 40% sucrose) sucrose density gradient (in tris-EDTA buffered saline at pH 7.4) at 100,000 g for 1.5 hrs. Buoyant density of the virus is 1.122 gm/ml and it sediments to the 25–40% sucrose interface.

6. The virus-containing band is separated and sonicated, using a Biosonic IV Sonic Oscillator for 10 sec. at low power, thereby breaking off viral protein from the TGEV. (The separated protein dissolves in the water phase.) The suspension may then be dialyzed against tris-EDTA buffered saline (pH 7.4) to remove sucrose.

7. The suspension containing the solubilized viral protein is subjected to isopycnic centrifugation through a continuous (10 to 60% sucrose) sucrose density gradient for 18–20 hours at 260,000 g. The TGE virus has a buoyant density of 1.18 gm/ml (approximately 42% sucrose). The desired protein band ("Band B") has a buoyant density of 1.02 to 1.03 gm/ml (6 to 8% sucrose). The Band B protein is recovered as an aqueous solution and used to prepare the vaccine.

8. The Band B solution is analyzed by nitrogen determination to obtain total protein content, so that the protein concentration can be adjusted to the level desired for vaccine preparation, such as approximately 1 mg/ml of total protein. This corresponds to approximately 0.5 mg/ml of SPA, which comprises about 50% of the Band B protein. The sucrose may be left in the solution or removed by dialysis. If the solution is to be frozen for storage the sucrose will act as a cryoprotectant.

9. As required, the protein concentration of the Band B solution can be increased by dialysis of the solution against polyethylene glycol, or decreased by addition of tris-saline buffer to give a concentration of approximately 1 mg/ml of total protein.

For a large scale commercial production of vaccines prepared in accordance with the present invention, the general procedure of this example can be followed, using a continuous flow density gradient centrifuge for the separation of step 7 to obtain the Band B protein. Alternatively, other protein separation and purification procedures can be used, such as ultrafiltration, reverse osmosis, and selective precipitation, such as isoelectric precipitation.

In another procedure, steps 1 to 4 of the foregoing example are carried out. The resuspended precipitate of the TGE virus is then treated with a non-ionic detergent to extract the protein. For example, Triton X-100 (Sigma Chemical Co., St. Louis, Mo.) or Nonidet P40 (BDH Chemicals, Ltd., Poola, England) can be added to the suspension to a concentration of 0.1% for the extraction. The resulting extract can then be processed by isopycnic centrifugation as described in step 7 of Example I, or by an alternative protein recovery procedure.

EXAMPLE II

To prepare an intramuscularly injectable vaccine from the Band B protein of Example I (step 9) or the subsequently isolated pure SPA protein, the viral protein is suspended in an aqueous solution of an aluminum hydroxide adjuvant. The vaccine should contain 1.0 milligrams (mg) of Band B protein per milliliter (ml), or 0.5 mg/ml of SPA. The aluminum hydroxide concentration can be adjusted to approximately 0.5% ($Al_2O_3$ basis). At the indicated concentrations of the Band B and SPA protein, a dose of approximately 2 milliliters should be used, thereby administering approximately 1.0 mg of SPA per dose.

For vaccination of sows, a two dose regimen can be used. The first dose may be given from several months to five to seven weeks prior to farrowing. For example, all of the sows may be vaccinated at one time in the Fall, such as around the first week in November. The second dose of the vaccine should be administered several weeks after the first dose, such as two to four weeks later, and may be given up to the time of farrowing. Alternatively, the SPA immunogen may be given as a single 2 ml dose, such as five to seven weeks prior to farrowing. However, a two-dose regimen is believed preferable for the most effective passive immunization of the baby pigs. All administrations may be given by intramuscular injection.

EXAMPLE III

For experimental purposes, Band B protein prepared as described in Example I was combined with Freund's complete adjuvant, using equal parts of the adjuvant and an aqueous solution of the Band B protein containing approximately 0.5 mg of SPA protein per ml. The Band B protein solution was also combined with an aluminum hydroxide adjuvant to prepare a vaccine containing approximately 0.5 mg of SPA protein per ml with an aluminum hydroxide concentration of 0.5% ($Al_2O_3$ basis). Both vaccines were used in approximately 2 ml dose amounts, in vaccine trials as summarized below.

Vaccine trials. Data from two vaccination trials with the TGE-SPA immunogen in bred sows are presented. In the first, one sow was immunized with the product administered with Freund's complete adjuvant initially, and with Freund's incomplete adjuvant in two booster inoculations. This animal farrowed three times. The second trial included four gilts immunized with TGE-SPA immunogen in the aluminum hydroxide adjuvant. These animals farrowed only once.

1. Sow 831—Freund's complete adjuvant.

A duroc first-litter gilt, seronegative for TGE, was immunized with 2 ml (approximately 1 mg) of TGE-SPA immunogen in Freund's complete adjuvant 6 weeks prior to farrowing. Two weeks prior to farrowing she received a booster inoculation of TGE-SPA immunogen in Freund's incomplete adjuvant.

a. Trial 1, 1st farrowing. The sow farrowed 13 piglets; all were very small. On the day following farrowing, the TGE antibody titer of her milk was 534; a serum titer was 178.

One-half of the piglets was orally challenged with 1 ml of Illinois TGE virus (50–100 PID$_{50}$) at 3 days of age; the other half was to acquire the disease naturally by exposure to infected littermates. None of the pigs showed signs of clinical TGE at any time after challenge, but all had serum antibodies when killed at 4½ months of age; no latent virus was detected at that time. Control pigs died of TGE following oral challenge.

b. Trial 2, 2nd farrowing. The sow was not immunized again prior to a second farrowing. At that time she had a serum TGE antibody titer of 38. Her colostral TGE antibody titer was 125 and that of her milk, 3 days later, was 34. The five piglets all developed clinical signs of TGE upon challenge with 50–100 PID$_{50}$ Illinois TGE virus. Two of the pigs (40%) died of the disease.

c. Trial, 3, 3rd farrowing. One month prior to farrowing the sow was given a booster immunization of TGE-SPA immunogen in Freund's incomplete adjuvant. Her serum titer at this time was 33. A granuloma appeared at the injection site. At the time of farrowing the serum TGE antibody titer was 231 and colostral antibody titer was greater than 625 (highest dilution). The antibody titer in milk at 5 days post-farrowing was 700.

None of the seven piglets in the litter developed clinical signs of TGE following oral challenge with 50–100 PID$_{50}$ Illinois isolant of TGE virus. Within 2 days after challenge of the piglets, the granuloma at the injection site of the sow had doubled in size.

Since no pigs had developed clinical TGE within 3 days after challenge with 50–100 PID$_{50}$, one piglet was given $5 \times 10^4$ PID$_{50}$ of Illinois isolant of TGE virus on the fourth day post-challenge. Clinical signs of TGE were not observed in either the challenged pig or in littermates. Diarrhea developed in some of the piglets prior to weaning (at about 2 weeks of age). The diarrhea was not typical of TGE, no other signs of disease were apparent and TGE virus could not be isolated from or identified in diarrhetic feces or from the animals themselves. Bacteria (flagellated short rods) were observed in the feces at copious concentration.

2. Aluminum hydroxide adjuvant. Six cross-bred firstlitter gilts, seronegative for TGE virus, were used in this experiment. Four were vaccinated at 5 weeks pre-farrowing with 1 mg of TGE-SPA immunogen aluminum hydroxide (0.5% Al$_2$O$_3$) and two served as controls. A second dose of immunogen was given to the four previously vaccinated gilts 2 weeks prior to farrowing. All of the piglets were challenged orally with 50–100 PID$_{50}$ of the Illinois isolant of TGE virus as a 10% gut slurry at 1 to 3 days post-farrowing.

The piglets on the tow control gilts, were showing signs of infection with TGE virus at 32 hours post-challenge. There was 100% morbidity in the two control litters. Three of nine pigs in one litter and one of eight in the other survived the infection, for a mortality rate of 76%.

No clinical signs of TGE were observed in piglets on two of the four vaccinated gilts. These litters consisted of nine piglets challenged at 1 day of age (Gilt 290) and six piglets challenged at 3 days of age (Gilt 294) with 50–100 PID$_{50}$ of Illinois isolant of TGE virus.

Mild clinical signs of TGE (e.g. light diarrhea) did develop in piglets of the remaining two litters on vaccinated gilts after the pigs were challenged with Illinois TGE virus (50–100 PID$_{50}$) at 3 (Gilt 291) and 2 (Gilt 433) days of age. The disease was characterized by light diarrhea in the nine piglets, appearing 56 hours post challenge. However, only one piglet died of TGE. (Three piglets died from causes unrelated to TGE infection). Two pigs died from causes other than TGE.

EXAMPLE IV

The SPA-containing Band B protein solution obtained in step 7 of Example I may be separated and further purified by gel filtration, using Sephadex G200. The gel filtration may be carried out with upward flow at a flow rate of 6 ml/hour using a tris-saline buffer. Two components are obtained as separate eluate fractions. The SPA is the second fraction to be eluted, and is the smaller of the two protein molecules contained in Band B. The recovered SPA protein may be further characterized by various procedures, such as polyacrylamide gel electrophoresis to obtain an Rf value corresponding to an apparent or actual molecular weight. The isoelectric point of the SPA protein can also be determined.

For example, the procedure for obtaining an Rf value can be used as described by Bishop and Roy, *J. Virol.*, 10, 234–243 (1972). In this procedure the polyacrylamide gel electrophoresis is carried out in the presence of sodium dodecyl sulfate (viz. 0.1% w/v) and urea (1.0 M). Using this procedure the SPA protein has an Rf value of $1.84\pm0.01$ (relative to human serum albumin). The other protein of Band B (which also has a buoyant density of 1.02 to 1.03 gm/ml) has a similarly determined Rf value of $1.40\pm0.01$. The presence of the sodium dodecyl sulfate assures determination of a charge-neutralized electrophoretic mobility (Rf value). The urea is used to cause the protein molecules to assume an "unwound" or more linear configuration thereby assisting the determination of an Rf value more nearly corresponding with true molecular weight. This procedure assumes, however, that the urea does not cause any alteration of protein size. The SPA protein as recovered by buoyant density separation is apparently decomplexed by the action of the urea. When polyacrylamide gel electrophoresis is carried out under the same conditions but in the absence of urea, the SPA protein has a charge-neutralized Rf value of $0.99\pm0.01$ (relative to bovine serum albumin). The molecular weight of the SPA protein calculated on the basis of its electrophoretic migration relative to that of bovine serum albumin (molecular weight=66,000) under these conditions is 67,000, which apparently, represents the SPA protein complex in its native state as it is released from the virion. The Rf value of $1.84\pm0.01$ determined in the presence of urea corresponds on the same basis to a calculated molecular weight of approximately 25,000.

The isolectric point of the SPA protein in its apparent native form (Rf $1.84\pm0.01$) has been determined by electrophoresis in a polyacrylamide gel containing commercial ampholyte of defined pH range, such as "Ampholine" manufactured by LKB. After the band containing SPA protein was cut out of the gel, its pH either was determined directly with a pH surface electrode or the band was eluted into distilled water and the pH was measured with a conventional dipping pH electrode. The isoelectric point of the SPA protein thus determined is pH 3.8. This information may be used in establishing conditions for absorption and elution of the SPA protein as a preparative method, according to well known procedures.

What is claimed is:

1. A vaccine for protecting swine against transmissable gastroenteritis (TGE), wherein the vaccine is in an injectable dose form including an adjuvant and is characterized by containing a protection-effective amount of a specific antigenic protein (SPA) which has been separated from TGE virus, said SPA being soluble in water and having a buoyant density of 1.02 to 1.03 grams per milliliters (gms/ml) as determined in aqueous sucrose, and being further characterized by its lactogenic immunizing property of protecting the baby pig offspring against TGE infection when administered to a TGE non-immune pregnant sow.

2. The vaccine of claim 1 in which said SPA is further characterized by having charge-neutralized electrophoretic mobilities (Rf values) relative to human serum albumin of 1.84±0.01 in the presence of urea and 0.99±0.01 in the absence of urea.

3. The vaccine of claim 1 in which said SPA is further characterized by having an isoelectric point of pH 3.8.

4. The vaccine of claim 1 in which each dose of said vaccine contains from 0.5 to 3.0 mg of said SPA.

5. The vaccine of claim 1 or claim 4 in which said vaccine is free of TGE virus.

6. The vaccine of claims 1, 4 or 5 in which the TGE-derived protein in said vaccine is composed substantially entirely of said SPA together with another viral protein of the same buoyant density.

7. The vaccine of claims 1, 4 or 5 in which the TGE-derived protein in said vaccine is composed substantially entirely of said SPA.

8. The method of protecting baby pig offspring against TGE infection, comprising administering a vaccine by injection to a TGE non-immune pregnant sow, said vaccine containing a swine immunizing specific antigenic protein (SPA) substantially free of transmissable gastroenteritis (TGE) virus and other TGE viral proteins characterized by being soluble in water and having a buoyant density of 1.02 to to 1.03 grams per milliliter (gms/ml) as determined in aqueous sucrose and being further characterized by its lactogenic immunizing property of protecting the baby pig offspring against TGE infection.

9. The method of claim 8 in which said SPA is further characterized by having charge-neutralized electrophoretic mobilities (Rf values) relative to human serum albumin of 1.84±0.01 in the presence of urea and 0.99±0.01 in the absence of urea.

10. The method of claim 8 in which said SPA is further characterized by having an isoelectric point of pH 3.8.

* * * * *